(12) United States Patent
Schleifer

(10) Patent No.: US 9,182,325 B2
(45) Date of Patent: Nov. 10, 2015

(54) METHOD AND APPARATUS FOR CHANGING RELATIVE CONCENTRATIONS OF GASES PRESENT WITHIN A GASEOUS SAMPLE FOR MASS SPECTROMETRY

(75) Inventor: Arthur Schleifer, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 2108 days.

(21) Appl. No.: 11/489,150

(22) Filed: Jul. 18, 2006

(65) Prior Publication Data

US 2008/0019879 A1    Jan. 24, 2008

(51) Int. Cl.
*G01N 33/00* (2006.01)
*B01L 5/00* (2006.01)
*G01N 1/40* (2006.01)
*B01L 3/00* (2006.01)

(52) U.S. Cl.
CPC ............. *G01N 1/4005* (2013.01); *B01L 3/5027* (2013.01)

(58) Field of Classification Search
CPC ........................... G01N 1/4005; B01L 3/5027
USPC .......... 95/43–56; 96/4–14; 436/173, 174, 178
See application file for complete search history.

(56) References Cited

U.S. PATENT DOCUMENTS 3,545,931 A * 12/1970 McKinley, Jr. ............... 436/113
3,772,909 A * 11/1973 Anderson ..................... 73/23.41
3,926,561 A * 12/1975 Lucero .......................... 436/178

OTHER PUBLICATIONS

Pinnau, Ingo and Toy, Lora G., "Gas and vapor transport properties of amorphous perfluorinated copolymer membranes based on 2,2-bistrifluoromethyl-4,5-difluoro-1,3-dioxole/tetrafluoroethylene", J. Membrane Science, vol. 109, 1996, pp. 125-133.

* cited by examiner

*Primary Examiner* — Paul Hyun
*Assistant Examiner* — Robert Eom

(57) ABSTRACT

An apparatus for changing relative concentrations of first and second analyte substances in an analyte sample comprises a sample cell defining a sample chamber therewithin, and a semipermeable boundary member disposed in the sample chamber to define first and second sides of the sample chamber. Sample flow input and sample flow output ducts direct an analyte sample containing respective initial concentrations of the first and second analyte substances into the first side of the sample chamber. The semipermeable boundary member permits diffusion therethrough of the first and second analyte substances to the second side of the sample chamber at different rates. An analyte sample in the second side of the sample chamber, and an analyte sample exiting the first side via the sample flow output duct, have respective concentrations of the first and second analyte substances that are different from the initial concentrations.

17 Claims, 1 Drawing Sheet

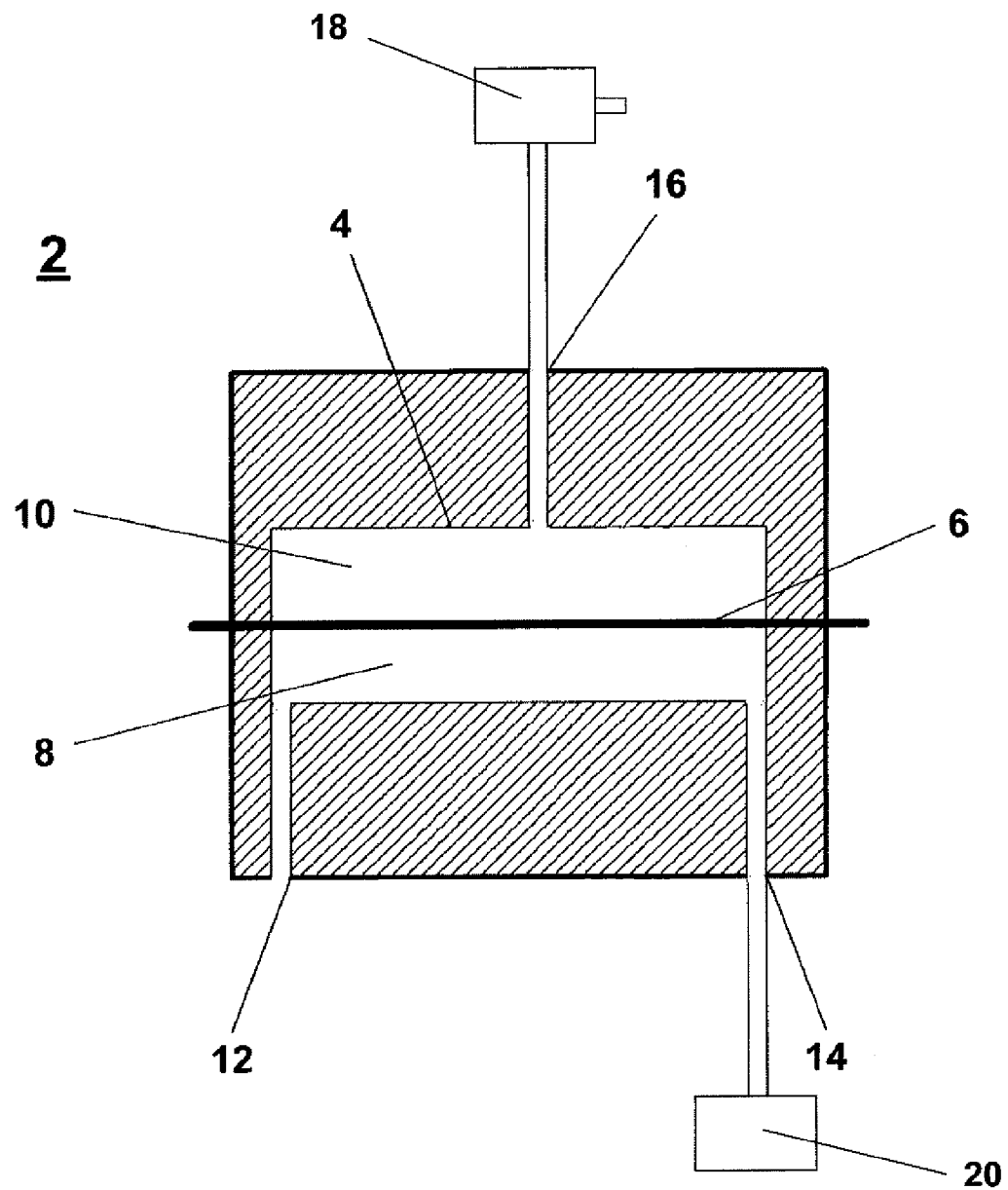

METHOD AND APPARATUS FOR CHANGING RELATIVE CONCENTRATIONS OF GASES PRESENT WITHIN A GASEOUS SAMPLE FOR MASS SPECTROMETRY

The research work described here was supported under the HSARPA agreement HSHQPA-04-9-0002 between the US Government and Agilent Technologies, Inc.

BACKGROUND OF THE INVENTION

The invention relates to mass spectrometry, and particularly to mass spectrometric analysis of gaseous analyte samples containing analyte substances of interest. The invention has applicability, among other areas, to analysis of atmospheric gas samples, and to detection of gaseous substances present in trace amounts.

The presence of normal concentrations of atmospheric gases in an analyte sample can interfere with measuring trace amounts of gases of interest. For example, when analyzing an atmospheric gas sample using a mass selective detector, the large amounts of nitrogen gas present in the atmosphere will cause a large peak, with tailing shoulder. This large signal can overwhelm the signal of a trace gas that is close in molecular weight to nitrogen.

Typically, the entire gas sample enters the analyzer without any separation. However, separation of the gas sample in order to reduce the concentration of the large-quantity gas relative to that of the trace gas of interest could improve the results of the analysis.

A gas chromatograph can be used to separate the gases prior to analysis by the mass spectrometer, but this is an expensive solution and is not easily incorporated into a remote field instrument.

SUMMARY OF THE INVENTION

An apparatus for changing relative concentrations of first and second analyte substances in an analyte sample comprises a sample cell defining a sample chamber therewithin, and a semipermeable boundary member disposed in the sample chamber to define first and second sides of the sample chamber. Sample flow input and sample flow output ducts direct an analyte sample containing respective initial concentrations of the first and second analyte substances into the first side of the sample chamber. The semipermeable boundary member permits diffusion therethrough of the first and second analyte substances to the second side of the sample chamber at different rates. An analyte sample in the second side of the sample chamber, and an analyte sample exiting the first side via the sample flow output duct, have respective concentrations of the first and second analyte substances that are different from the initial concentrations.

Further features and advantages of the present invention, as well as the structure and operation of preferred embodiments of the present invention, are described in detail below with reference to the accompanying exemplary drawings.

BRIEF DESCRIPTION OF THE DRAWINGS

FIG. 1 is a cross-sectional diagram of an apparatus embodying the invention.

DETAILED DESCRIPTION

An apparatus or method embodying the invention can selectively separate different gases based on factors such as molecular weight, molecular size (which takes into consideration molecular weight and spatial configuration), and electrical composition. Selective separation that employs such factors to distinguish different analyte gases, such as ambient background atmospheric gases and a trace gas of interest allows for the separation of a greater percentage of the background gases compared to the trace gases of interest. Thus, analysis of one or more of the analyte gases, such as detection of the presence of an analyte substance of interest, mass spectrographic analysis, quantitative measurement of one or more of the analyte substances, etc., is facilitated.

FIG. 1 is a cross-sectional diagram of a structure embodying the invention. A sample cell 2 defines therewithin a sample chamber 4, and also includes a semipermeable boundary member (also referred to herein simply as "boundary member") shown as a semipermeable membrane (also referred to herein simply as "membrane") 6. The membrane 6 divides the sample chamber 4 into a first side 8 and a second side 10. The first side 8 has a sample flow input duct 12 and a sample flow output duct 14. An analyte sample which is to be analyzed, and which contains multiple analyte substances at respective initial concentrations, enters the first side 8 of the sample chamber 4, through the input duct 12. After processing, the processed analyte sample exits through the output duct 14 and is analyzed using an analyzer 20 which is connected to the output duct 14.

In operation, analyte substances within the analyte sample in the first side 8 migrate through the membrane 6 into the second side 10. As will be described below, the various analyte substances migrate at different rates. As a consequence, the relative concentrations of the analyte substances change.

The second side 10 may initially contain ambient atmospheric gas, or other initial gaseous substance. The second side 10 has an access duct 16, which may be coupled to a pump 18 for either increasing or decreasing the pressure within the second side 10, in an embodiment in which active gas migration due to differential pressure is employed. In particular, decreasing the pressure of the second side 10, relative to that of the first side 8, causes a pressure differential that facilitates the migration of the analyte substances, at their respective different rates, from the first side 8 through the membrane 6 to the second side 10.

Optionally, a second access duct (not shown) may be provided, if it is desired to facilitate separate gas input and output to the second side 10. For instance, in one such embodiment, gas flows through the access duct 16 and the second access duct, thereby flowing into and out of the second side 10.

Suitable valves (not shown) are provided for opening and closing the ducts 12, 14, and 16 to facilitate operation as described herein.

The sample to be processed is an analyte sample gas, which comprises first and second analyte substances. For instance, the sample might be a sample of atmosphere, containing a trace quantity of a gaseous substance of interest, e.g., whose presence is to be detected. The gaseous substance of interest might include an atmospheric pollutant, a trace vapor of a substance whose presence is to be detected, a deployed chemical weapon, etc. For purposes of discussion, the atmospheric component such as nitrogen will be treated as an example of a first analyte substance. Likewise, the trace substance to be detected shall be treated as an example of a second analyte substance.

With reference to a given sample, such as the atmospheric sample just described, the boundary member is characterized as semipermeable, in that its permeability varies with respect to different substances within the sample. For instance, the permeability of atmospheric components such as nitrogen (cited above) might be greater than its permeability with reference to the trace substance to be detected, such as a higher-molecular weight organic vapor, etc.

Processing, as referred to above, includes a migration of one or both of the first and second analyte substances through the semipermeable boundary member. The migration can take place passively, for instance by diffusion. Alternatively, the migration can be driven, for instance by a pressure differential between the first and second sides 8 and 10 of the sample chamber 2. In one embodiment, a vacuum pump (not shown) can be used to reduce the pressure inside the second side 10, so as to draw gaseous analyte substances through the membrane 6. Other pressure differential arrangements may also be used, such as changing the pressure on either the first side 8 or the second side 10, and either increasing or decreasing the pressure in either the first side 8 or the second side 10, or any combination thereof.

The rate at which the first analyte substance migrates through the boundary member is different from the rate at which the second analyte substance migrates through the semipermeable boundary member. In some cases, one of the analyte substances might not diffuse through the boundary member at all, or might do so only at a negligible rate. In other cases, both the first and second analyte substances migrate through the boundary member, but at known, different rates. For a given sample, containing known first and second analyte substances, a boundary member may be chosen, made of a material having known, different, rates of migration for the first and second analyte substances to be analyzed.

In one embodiment, employing a membrane for which different migration rates for a given combination of analyte gases are known, and in which such migration takes place over a specified time, a predictable change in the relative concentrations of analyte gas substances can be ascertained.

In another embodiment, sensors (not shown) may be provided within the first and/or second sides 8 and 10 of the sample chamber 4. In a "closed loop" mode of operation, the sensors monitor the concentrations of analyte substances, and the processing within the sample chamber 4 runs until desired absolute or relative concentrations are achieved.

The concentrations of the two analyte substances on the input and output sides, after the above-described processing by migration, will be different from the initial concentrations. Subsequent analytical tests may be made on the analyte, whose test results will reflect the relative change in concentrations. For instance, a test for presence of the second analyte substance, which is sensitive to the first analyte substance, may be performed after the concentration of the first analyte substance is decreased, relative to that of the second analyte substance.

For example, nitrogen inevitably will be abundant in an atmospheric sample. When an atmospheric sample is analyzed in a mass spectrometer, without any prior chromatographic separation or other change in relative concentrations of its constituent analyte substances, the nitrogen might overwhelm any signal of trace analyte substances. By first reducing the percentage of the nitrogen, relative to that of other gaseous components of the sample, measurement of the trace amounts of other compounds within the sample is facilitated.

As the analyte sample passes through the first side 8 of the sample chamber 4, the nitrogen will pass across the membrane 6 at a much faster rate than that of many other analyte sample substances of interest. The rate of this transfer will be related to the differential pressure from the first side 8 to the second side 10. The amount of nitrogen that passes across the membrane 6 will be directly related to the area of the membrane 6, and to the differential pressure across the membrane.

The degree to which the relative concentrations of the analyte substances change will also be related to the rate at which the sample flows across the membrane 6. The greater the rate differential, the greater the change in relative concentrations.

The result will be that much of the atmospheric nitrogen will have migrated to the second side 10. Such nitrogen can then simply be dumped out of the access duct 16, into the ambient atmosphere, or pumped out by the aforementioned differential pressure pump. What remains within the first side 8 is a gas analyte sample relatively depleted of nitrogen. The sample is then removed from the firs side 8, and subjected to desired analysis, such as mass spectrometry.

The test results will then better reflect the presence of the first analyte substance, and be less influenced by the second analyte substance. This is of value, for instance, when the analyte substance being tested for is in trace quantities, and would only produce a small-magnitude signal of its presence.

An apparatus or method embodying the invention is an alternative to a conventional gas chromatograph. Such a method or apparatus is much less expensive, and requires little maintenance. It is not necessary to remove all of the background gases, but merely enough so that the smaller signals of the analyte substance, present in trace amounts and being tested for, can be detected.

One embodiment of the device is constructed such that a Teflon AF (trademark) membrane separates the two sides of the sample chamber of a sample cell. One side is the sample gas mixture under test that will enter the mass analyzer. The other side of the Teflon AF membrane is exposed to a vacuum source. Teflon AF is described in Pinnau et al., "Gas and vapor transport properties of amorphous perfluorinated copolymer membranes based on 2,2-bistrifluoromethyl-4,5-difluoro-1,3-dioxole/tetrafluoroethyline," Journal of Membrane Science 109 (1996), pp. 125-133.

As the gas mixture enters the cell 2, the different pressures on the sides 8 and 10 of the membrane 6 will pull different analyte gases across the membrane 6 to migrate through the membrane 6 at different rates. These rate differences can be from a factor of 2-5, and can be as much as a factor of 10 or more. This differential removal of background gases will allow for smaller/trace gases to be detected. The amount of background gases that will be removed depends on factors such as the area of exposed membrane, composition and thickness of membrane, the time duration during which the migration is allowed to run, and the differential pressure across the membrane.

Although the present invention has been described in detail with reference to particular embodiments, persons possessing ordinary skill in the art to which this invention pertains will appreciate that various modifications and enhancements may be made without departing from the spirit and scope of the claims that follow.

What is claimed is:

1. An apparatus for changing relative concentrations of first and second analyte substances in an atmospheric analyte sample to facilitate analysis of one of the analyte substances, the apparatus comprising:

a sample cell, defining therewithin a sample chamber;

a semipermeable boundary member disposed in the sample chamber to define first and second sides of the sample chamber;

a sample flow input duct for directing the atmospheric analyte sample containing respective initial concentrations of the first and second analyte substances into the first side of the sample chamber;

a sample flow output duct for directing the atmospheric analyte sample containing respective final concentrations of the first and second analyte substances out of the first side of the sample chamber; and an analyzer connected to the sample flow output duct for analyzing the first and second analyte substances;

wherein the semipermeable boundary member permits migration therethrough of the first and second analyte substances to the second side of the sample chamber at different rates so that the analyte sample exiting the first side via the sample flow output duct has relative final concentrations of the first and second analyte substances that are different from the relative initial concentrations;

wherein the apparatus is configured to direct an atmospheric sample comprising the initial concentrations of the first and second analyte substances through the sample flow input duct and to analyze the final concentrations of the first and second analyte substances that exit the first side via the sample flow output duct.

2. The apparatus of claim 1, wherein:

the analyte sample comprises a predetermined first analyte substance and a predetermined second analyte substance and is to have its relative concentrations thereof changed; and the semipermeable boundary member has a predetermined difference between its migration rate for the first analyte substance and its migration rate for the second analyte substance.

3. The apparatus of claim 1, wherein:

the first analyte substance is an atmospheric component, and the second analyte substance is a trace substance of interest, the first analyte substance being in higher initial concentration, relative to the initial concentration of the second analyte substance; and the semipermeable boundary member permits migration of the atmospheric component at a faster rate than a rate of migration of the trace substance of interest.

4. The apparatus of claim 3, wherein the first analyte substance is nitrogen.

5. The apparatus of claim 1, wherein the semipermeable boundary member comprises a perfluorinated copolymer.

6. The apparatus of claim 1, further comprising:

a second side duct, providing access to the second side of the sample chamber; and a pump, coupled to one of (i) the sample flow input duct, (ii) the sample flow output duct, and (iii) the second side duct, for creating a pressure differential between the first side and the second side.

7. The apparatus of claim 6, wherein the pump is coupled to the second side duct, and reduces the pressure within the second side, relative to the pressure within the first side.

8. A method for analyzing an analyte substance in an atmospheric analyte sample, the method comprising:

entering the atmospheric analyte sample into a first side of a sample chamber via a sample flow input duct, the sample chamber comprising a second side and a semipermeable boundary member separating the first and second sides;

migrating the analyte substance and an atmospheric component of the atmospheric analyte sample through the semipermeable boundary member to the second side at different rates, thereby reducing the concentration of the atmospheric component relative to the concentration of the analyte substance within the first side of the sample chamber, extracting from the first side of the sample chamber the analyte sample, and analyzing the analyte substance in the extracted analyte sample.

9. The method of claim 8, wherein the migrating includes applying a differential pressure between the first and second sides.

10. The method of claim 9, wherein the applying a differential pressure includes employing a pump, coupled to the second side, to reduce the pressure within the second side, relative to the pressure within the first side.

11. The method of claim 8, wherein the analyzing is performed using a mass spectrometer.

12. The apparatus of claim 1, wherein the analyzer comprises a mass spectrometer.

13. The method of claim 8, wherein:

the atmospheric analyte sample comprises a predetermined analyte substance and a predetermined atmospheric component; and the semipermeable boundary member has a predetermined difference between the migration rates of the analyte substance and the atmospheric component.

14. The method of claim 8, wherein the atmospheric component is nitrogen.

15. The method of claim 8, wherein the semipermeable boundary member comprises a perfluorinated copolymer.

16. The method of claim 8, further comprising:

collecting the atmospheric analyte sample from the atmosphere and introducing the analyte sample into the sample flow input duct prior to the entering.

17. The method of claim 8, further comprising:

monitoring the concentrations of the analyte substance and atmospheric component in the first side until desired relative concentrations are achieved, prior to the extracting.

* * * * *